United States Patent
Tanaka et al.

(10) Patent No.: US 8,575,142 B2
(45) Date of Patent: *Nov. 5, 2013

(54) AGENT FOR IMPROVING INSULIN RESISTANCE

(75) Inventors: Miyuki Tanaka, Kanagawa (JP); Eriko Misawa, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 1253 days.

This patent is subject to a terminal disclaimer.

(21) Appl. No.: 11/917,870

(22) PCT Filed: Sep. 22, 2006

(86) PCT No.: PCT/JP2006/318815
§ 371 (c)(1),
(2), (4) Date: Dec. 17, 2007

(87) PCT Pub. No.: WO2007/043306
PCT Pub. Date: Apr. 19, 2007

(65) Prior Publication Data
US 2009/0131388 A1 May 21, 2009

(30) Foreign Application Priority Data
Sep. 30, 2005 (JP) .................................. 2005-287886

(51) Int. Cl.
*A61K 31/575* (2006.01)
*A61K 47/00* (2006.01)
*C07J 9/00* (2006.01)

(52) U.S. Cl.
USPC ............ 514/182; 514/170; 552/547; 424/439

(58) Field of Classification Search
USPC .................... 552/547; 424/439; 514/170, 182
See application file for complete search history.

(56) References Cited

U.S. PATENT DOCUMENTS 4,598,069 A * 7/1986 Hikino et al. .................... 514/54

FOREIGN PATENT DOCUMENTS

| CN | 1557324 | 12/2004 |
|---|---|---|
| JP | 60-214741 | 10/1985 |
| JP | 08-208495 | 8/1996 |
| JP | 10-036283 | 2/1998 |
| JP | 2000-319190 | 11/2000 |
| JP | 2003-286185 | 10/2003 |
| JP | 2005-068132 | 3/2005 |
| WO | WO 03/020026 | 3/2003 |
| WO | WO2004100969 | * 11/2004 |
| WO | WO 2005/094838 | 10/2005 |
| WO | WO 2005/095436 | 10/2005 |
| WO | WO 2006/035525 | 4/2006 |

OTHER PUBLICATIONS

Itoh et al., "Sterols of Liliaceae." Phytochemistry, 16(1), 140-1, 1977 (Abstract only).*
Ajabnoor, "Effect of Aloes on Blood Glucose Levels in Normal and Alloxan Diabetic Mice." Journal of Ethnopharmacology, vol. 28, pp. 215-220, 1990.*
Itoh, et al. "Four New and Other 4α-Methylsterols in the Seeds of Solanaceae," *Phytochemistry*, vol. 17, No. 5, pp. 971-977, 1978.
Okyar, et al. "Effect of *Aloe vera* Leaves on Blood Glucose Level in Type I and Type II Diabetic Rat Models," *Phytotherapy Research*, vol. 15, No. 2, pp. 157-161, 2001.
Rajasekaran, et al. "Hypoglycemic Effect of *Aloe vera* Gel on Streptozotocin-Induced Diabetes in Experimental Rats," *Journal of Medicinal Food*, vol. 7, No. 1, pp. 61-66, 2004.
Tanaka, et al. "Identification of Five Phytosterols from *Aloe vera* Gel as Anti-Diabetic Compounds," *Bio. Pharm. Bull*, vol. 29, No. 7, pp. 1418-1422, 2006.
Yeh, et al. "Systematic Review of Herbs and Dietary Supplements for Glycemic Control in Diabetes," *Diabetes Care*, vol. 26, No. 4, pp. 1277-1294, 2003.
Yongchaiyudha, et al. "Antidiabetic Activity of *Aloe vera* L. Juice, I. Clinical Trial in New Cases of Diabetes Mellitus," *Phytomedicine*, vol. 3, No. 3, pp. 241-243, 1996.
International Search Report dated Dec. 18, 2006.
Supplementary European Search Report dated Jul. 29, 2011 issued to related European application No. EP 06 81 0428.

* cited by examiner

*Primary Examiner* — Barbara P Badio
(74) *Attorney, Agent, or Firm* — Knobbe, Martens, Olson & Bear LLP

(57) ABSTRACT

To inhibit production of adipocytokines, in particular, adipocytokines that elicit insulin resistance and to prevent onset of pathosis caused by the insulin resistance or ameliorate the pathosis, the present invention provides an agent or a food or drink which contains a compound having a lophenol skeleton, or an organic solvent extract or a hot water extract of a Liliaceae plant or, a fraction thereof containing the compound as an active ingredient.

2 Claims, 1 Drawing Sheet

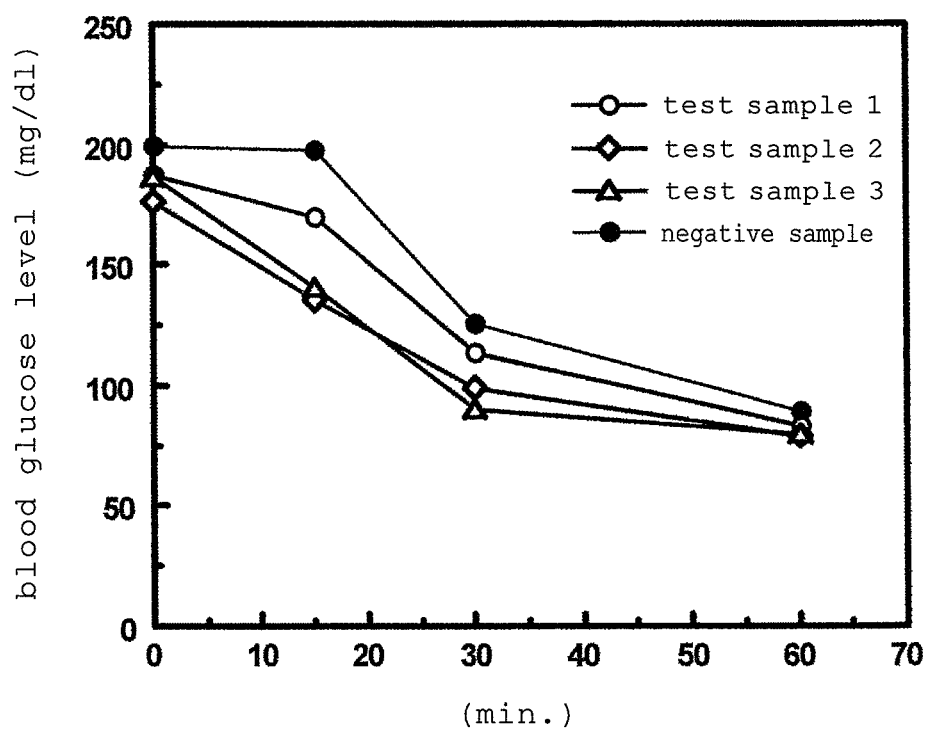

AGENT FOR IMPROVING INSULIN RESISTANCE

CROSS-REFERENCE TO RELATED APPLICATIONS

This application is the U.S. National Phase under 35 U.S.C. §371 of International Application PCT/JP2006/318815, filed Sep. 22, 2006, which was published in a non-English language, which claims priority to JP 2005-287886, filed Sep. 30, 2005.

TECHNICAL FIELD

The present invention relates to an agent for improving insulin resistance, which contains a compound having a lophenol skeleton as an active ingredient, and food or drink containing the same. In particular, the present invention relates to an agent for improving insulin resistance, which has an effect of controlling production of adipocytokines that are factors involved in onset and severity of pathosis that the insulin resistance plays a role therein, such as free fatty acid, plasminogen activator inhibitor, tumor necrosis factor, monocyte chemoattractant protein-1, and resistin, and relates to a food or drink containing the same.

BACKGROUND ART

Insulin is a kind of hormones which is produces by β-cells in Langerhans islets of the pancreas. Insulin acts on lipid metabolism and protein metabolism as well as sugar metabolism via insulin receptors which are present in target tissues of insulin such as skeletal muscles, liver, and fats, and plays an important role in maintaining homeostasis of living bodies. Examples of the effects of insulin on respective target tissues include promotion of incorporation of glucose from blood into muscle cells and adipocytes, promotion of glycogen production in liver and muscle tissues, inhibition of gluconeogenesis in liver, promotion of glucose consumption and fatty acid synthesis in adipocytes, and inhibition of decomposition of lipids.

The insulin resistance means a state where the cells, organs, or individuals require larger amounts of insulin than those typically required in order to obtain the respective effects of insulin, that is, an insulin effect incompetent state where sensitivity to insulin is reduced. From the results of past epidemiologic investigations, hypertension, diabetes, hyperlipidemia (hypertriglyceridemia and hypo-HDL-cholesterolemia), obesity, and the like are considered as pathosis caused by the insulin resistance. The insulin resistance causes insufficient effects of insulin on the sugar metabolism, which results in compensatory hyperinsulinemia for maintaining blood sugar level, whereby hyperglycemia and glucose intolerance occur and diabetes is promoted by exhaustion of pancreatic β-cells. In addition, the hyperinsulinemia enhances activation of sympathetic nerves and accelerates sodium absorption of kidney to cause hypertension, and also induces postprandial hyperlipidemia and hyperuricemia, an increase in plasminogen activator inhibitor-1 (PAI-1), and the like.

Meanwhile, the insulin resistance induces abnormal lipid metabolism caused by the insufficient effects of insulin, and free fatty acid (FFA) released from adipocytes increases in liver to accelerate synthesis of triglyceride (TG) therein, resulting in hypertriglyceridemia. In addition, activity of lipoprotein lipase (LPL) generally having high insulin sensitivity is reduced in the insulin resistant state, so decomposition of TG reduces and the hypertriglyceridemia is additionally aggravated. Further, progression of diabetes causes onset of complications such as retinopathy, nephropathy, and gangrene caused by angiopathy so that myocardial infarction and cerebral infarction that are arterioscleotic diseases proceed, and hypertension promotes cardiovascular diseases. As described above, the insulin resistance is considered to be significantly involved in aggravation of complication of pathosis (Non-patent Document 1).

In recent years, analysis of organ-specific gene expression has been conducted. As a result, it was found that various physiologically active substances are secreted from fat tissues, and the fat tissues thus have been recognized to be, not only energy storage tissues, but also the largest endocrine organ in a living body. Endocrine factors derived from the fat tissues have a generic name "adipocytokines" and play important roles in maintenance of homeostasis in metabolism. It is considered that an excessive or a too small amount of adipocytokines are produced and secreted in a case of obesity, that is, a state where fats are accumulated, and the balance of the adipocytokines is disrupted, resulting in insulin resistance.

The adipocytokines are classified into two groups: one that enhances insulin sensitivity; and one that elicits insulin resistance. Representative examples of the former group include adiponectin, leptin, and AMP-dependent protein kinase (AMPK) and the like. In particular, adiponectin has been reported to have an effect of canceling insulin resistance and an effect of inhibiting gluconeogenesis in liver (Non-patent Document 2).

Meanwhile, examples of the adipocytokines that elicit insulin resistance include, in addition to the aforementioned FFA and PAI-1, tumor necrosis factor-α (TNF-α), monocyte chemoattractant protein-1 (MCP-1) that is a kind of inflammatory chemokine, and resistin. In particular, TNF-α has been reported to have an effect of inhibiting tyrosine phosphorylation of an insulin receptor and IRS1 (insulin receptor substrate 1) in the insulin signal transduction mechanism so that the effect of insulin is attenuated, whereby insulin resistance is elicited. In addition, there is a report that, in the insulin resistant state, the MCP-1 level in a living body increases and mRNA of GLUT4 (glucose transporter-4) that is a glucose-transporting carrier, PPARγ (peroxisome proliferator-activated receptor γ) that is an intranuclear receptor, β3AR (β3-adrenergic receptor) that is a kind of β catecholamine receptor of an adipocyte, and aP2 (adipocyte fatty-acid-binding protein 2) that is a fatty acid-binding protein reduces. Thus, MCP-1 is considered to be a causative agent that reduces insulin sensitivity (Non-patent Documents 3, 4, and 5).

As agents for improving insulin resistance, biguanide agents that inhibit gluconeogenesis mainly in liver and thiazolidine derivatives for improving insulin sensitivity of muscles and fat tissues have been developed. Those agents have already been permitted as diabetic medicines, and also used for treatment of arterioscleerotic disease. The thiazolidine derivatives typified by troglitazone and pioglitazone are each considered to act as a ligand for a peroxisome proliferator-activated receptor (PPAR) that is an intranuclear receptor-type transcription factor to promote differentiation of adipocytes, thereby improving insulin resistance.

In addition, an agent for improving insulin resistance containing adiponectin or their genes as an active ingredient (Patent Document 1), a preventive and/or therapeutic agent for diseases due to insulin resistance, which contains as an active ingredient a substance having affinity to bombesin receptor subtype 3 (BRS-3) (Patent Document 2), a free fatty acid (FFA) reducing agent containing as an active ingredient a pyrrole derivative (Patent Document 3) and the like have been disclosed as the agents for improving insulin resistance. Further, a composition for improving insulin resistance containing, as an active ingredient, acetic acid and an ion or salt thereof (Patent Document 4), an agent for improving insulin resistance containing a fatty oil which contains particular diglyceride and/or monoglyceride (Patent Document 5) and the like have been disclosed as the agents containing as an active ingredient a substance derived from food or drink.

Plant sterols such as β-sitosterol, campesterol, stigmasterol have been known to have a reducing effect on blood cholesterol by inhibition of absorption of the cholesterol, and practical use thereof has been attempted by adding them as a fat composition to edible oil. In addition, there are disclosed an anti-obesity agent and a lipid metabolism-improving agent containing as an active ingredient a cholestenone compound which is synthesized by using as a starting material the plant sterols such as β-sitosterol and campesterol (Patent Documents 6 to 8, and Non-patent Document 6).

Further, there is disclosed an agent for promoting adiponectin secretion containing: an extract derived from at least one of rice bran, shimeji mushroom, chrysanthemum, rye, white birch, and Spanish Jasmine (*Alpinia zerumber*), and cycloartane type triterpene or cycloartenol and/or (24S)-24, 25-dihydroxycycloartanol which are derivatives thereof (Patent Document 9).

The plants belonging to the genus *Aloe* of Liliaceae are a group of plants including *Aloe vera* (*Aloe barbadensis* Miller), *Aloe arborescens* (*Aloe arborescens* Miller var. *natalensis Berger*), and the like, and have been known to have various effects from experience. For example, there are disclosed an immunodepression-improving agent containing a butanol fraction of an aloe extract or aloin (Patent Document 10), agents related to improving blood glucose level (Patent Documents 11 to 14), and a preventive and improving agent for obesity (Patent Document 15) and the like, but the improving action on insulin resistance of the plants belonging to the genus *Aloe* has not been reported.

[Patent Document 1] International Publication NO. WO 2003/63894
[Patent Document 2] Japanese Patent Laid-open No. 10-298100
[Patent Document 3] Japanese Patent Laid-open No. 08-12573
[Patent Document 4] Japanese Patent Laid-open No. 2002-193797
[Patent Document 5] Japanese Patent Laid-open No. 2001-247473
[Patent Document 6] Japanese Patent Laid-open No. 07-165587
[Patent Document 7] Japanese Patent Laid-open No. 11-193296
[Patent Document 8] Japanese Patent Laid-open No. 2001-240544
[Patent Document 9] Japanese Patent Laid-open No. 2005-68132
[Patent Document 10] Japanese Patent Laid-open No. 08-208495
[Patent Document 11] Japanese Patent Laid-open No. 60-214741
[Patent Document 12] Japanese Patent Laid-open No. 2003-286185
[Patent Document 13] U.S. Pat. No. 4,598,069
[Patent Document 14] U.S. Patent Application Publication No. 2003/0207818
[Patent Document 15] Japanese Patent Laid-open No. 2000-319190
[Non-patent Document 1] Insulin resistance and lifestyle-related diseases, Ed. Kazuaki Shimamoto, Shindan to Chiryo Company, 2003, pp. 1-5
[Non-patent Document 2] Adiposcience, 1(3), 2004, pp. 247-257
[Non-patent Document 3] Proceedings of the National Academy of Sciences, vol. 100, 2003, pp. 7265-7270
[Non-patent Document 4] Nature, vol. 389, 1997, pp. 610-614
[Non-patent Document 5] The Netherlands Journal of Medicine, 6(6), 2003, pp. 194-212
[Non-patent Document 6] Hormone Metabolism Research, vol. 37, 2005, pp. 79-83

DISCLOSURE OF THE INVENTION

With use of the biguanide agent that is a conventional agent for improving insulin resistance, gastrointestinal dysfunction or, rarely lactic acidosis may sometimes occur. In addition, a thiazolidine derivative that is the same kind of the agent may sometimes cause severe side effects such as fluid retention, increase in body weight and liver dysfunction, so use thereof requires additional attention. Further, for the insulin resistance in states other than diabetes or hyperglycemia, it has been practically difficult to use antidiabetic agents. Under such circumstances, a development of a functional material which is excellent in safety, can be ingested on a daily basis, and can efficiently improve the insulin resistance with pain as little as possible has been desired.

In view of the aforementioned problems, the inventors of the present invention have investigated mechanisms of the insulin resistance involved in the lifestyle-related diseases, such as hypertension, diabetes, hyperlipidemia including hypertriglyceridemia and high density lipoprotein hypocholesterolemia, and obesity, and have investigated an agent relating to prevention, amelioration, and the like of the diseases, that is, an agent for improving insulin resistance. The inventors of the present invention have made attention to adipocytokines that are factors involved in onset and exacerbation of the insulin resistance, and have made extensive investigation on a novel functional material capable of improving the insulin resistance by controlling the aforementioned factors. As a result, the inventors of the present invention have found that a compound having a lophenol skeleton has a controlling effect on production of adipocytokines such as free fatty acid, TNF-α and MCP-1, in particular, efficient reducing effect on the production of an adipocytokine that elicits the insulin resistance, and the insulin resistance is improved by the action.

As compared with the aforementioned effects of the present invention, Patent Document 9 only describes a preventive effect of the plant extract on differentiation of cultured adipocytes, and a promotion effect of ergosterol on secretion of adiponectin, and there was no description nor suggestion of the improving effect of the active ingredient of the present invention on the insulin resistance.

In addition, the inventors of the present invention found that, by investigating using an insulin tolerance test in addition to the glucose clamp method, the steady state plasma glucose (SSPG) method and the minimal model method which are conventional methods of evaluating the insulin resistance, the compound having a lophenol skeleton more directly improves the insulin resistance without intervention of insulin secretion property or the like.

The insulin tolerance test has not been performed in the aforementioned Patent Documents 1 to 5. The inventors of the present invention found a more advantageous effect of the compound having a lophenol skeleton, which improves the insulin resistance without being affected by the insulin secretion property or the like and which is extremely advantageous as compared with the conventional improving effects on insulin resistance, and the present invention thus has been completed.

An object of the present invention is to provide an agent for improving insulin resistance, which contains a compound having the lophenol skeleton as an active ingredient. In addition, another object of the present invention is to provide a physiologically functional food or drink such as food for specified health uses containing the agent for improving insulin resistance.

First invention of the present application to solve the aforementioned problems is an agent for improving insulin resistance, containing a compound represented by the following general formula (1) as an active ingredient.

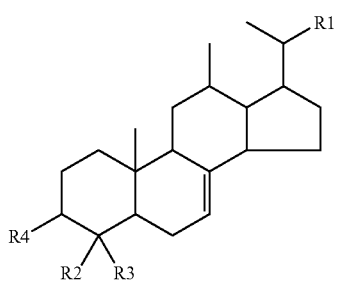

(1)

(In the formula, R1 represents an alkyl group, or an alkenyl group having 1 or 2 double bonds, or a substituted alkyl or alkenyl group having a hydroxyl group and/or a carbonyl group, which is straight or branched chain having 5 to 16 carbon atoms, R2 and R3 each independently represent a hydrogen atom, an alkyl group or a substituted alkyl group having 1 to 3 carbon atoms and R4 forms C=O with the carbon atom constituting the ring or represents —OH or —OCOCH$_3$.)

Further, the following 1) to 4) are preferred embodiments.

1) In the aforementioned compound, one of R2 and R3 is a hydrogen atom, the other is methyl group, and R4 is a hydroxyl group.

2) In the aforementioned 1), R1 is represented by any one of the following formulas:

—CH$_2$—CH$_2$—CH(—CH$_2$—CH$_3$)—CH(CH$_3$)$_2$

—CH$_2$—CH$_2$—CH=C(CH$_3$)$_2$

—CH$_2$—CH=C(CH$_3$)—CH(CH$_3$)$_2$

—CH$_2$—CH$_2$—C(=CH—CH$_3$)—CH(CH$_3$)$_2$

—CH$_2$—CH$_2$—CH(Ra)=C(CH$_3$)Rb (wherein Ra and Rb is any of —H, —OH, or —CH$_3$)

—CH$_2$—CH$_2$—CH(Rc)—CH(CH$_3$)Rd (wherein Rc and Rd is any of —H, —OH, or —CH$_3$)

3) The aforementioned compound described in 2) is selected from the group consisting of 4-methylcholest-7-en-3-ol, 4-methylergost-7-en-3-ol and 4-methylstigmast-7-en-3-ol.

4) The aforementioned compound described in 1) to 3) is contained in an amount of at 1 least 0.001% by mass.

Second invention of the present application to solve the aforementioned problems is an agent for improving insulin resistance, containing an organic solvent extract or a hot water extract of a Liliaceae plant or a fraction thereof, which contains a compound represented by the following general formula (1), and in which the organic solvent extract or the hot water extract of the Liliaceae plant, or the fraction thereof contains as an active ingredient a composition containing at least 0.001% by dry mass of the compound represented by the following general formula (1).

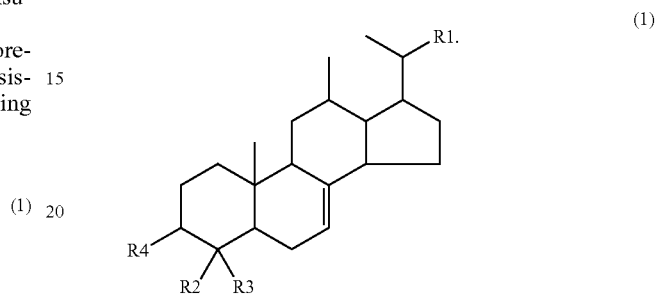

(1)

(In the formula, R1 represents an alkyl group, or an alkenyl group having 1 or 2 double bonds, or a substituted alkyl or alkenyl group having a hydroxyl group and/or a carbonyl group, which is straight or branched chain having 5 to 16 carbon atoms, R2 and R3 independently represent a hydrogen atom, an alkyl group or a substituted alkyl group having 1 to 3 carbon atoms, and R4 forms C=O with the carbon atom constituting the ring or represents —OH or —OCOCH$_3$.)

Further, the following 5) to 7) are preferred embodiments.

5) In the aforementioned compound, one of R2 and R3 is a hydrogen atom, the other is methyl group, and R4 is a hydroxyl group.

6) In the aforementioned 5), R1 is represented by any one of the following formulas:

—CH$_2$—CH$_2$—CH(—CH$_2$—CH$_3$)—CH(CH$_3$)$_2$

—CH$_2$—CH$_2$—CH=C(CH$_3$)$_2$

—CH$_2$—CH=C(CH$_3$)—CH(CH$_3$)$_2$

—CH$_2$—CH$_2$—C(=CH—CH$_3$)—CH(CH$_3$)$_2$

—CH$_2$—CH$_2$—CH(Ra)=C(CH$_3$)Rb (wherein Ra and Rb is any of —H, —OH, or —CH$_3$)

—CH$_2$—CH$_2$—CH(Rc)—CH(CH$_3$)Rd (wherein Rc and Rd is any of —H, —OH, or —CH$_3$)

7) The aforementioned compound described in 6) is selected from the group consisting of 4-methylcholest-7-en-3-ol, 4-methylergost-7-en-3-ol and 4-methylstigmast-7-en-3-ol.

Third invention of the present application to solve the aforementioned problems is food or drink containing the aforementioned agent for improving insulin resistance according to the first or second invention.

In addition, the following 8) is a preferred embodiment.

8) The food or drink contains the compound represented by the aforementioned general formula (1) in an amount of 0.0001% by mass or more.

Fourth invention of the present application to solve the aforementioned problems is use of a compound represented by the aforementioned general formula (1), or an organic solvent extract or hot water extract of a Liliaceae plant, or a fraction thereof which contains at least 0.001% by dry mass of the compound for production of an agent for improving insulin resistance.

Fifth invention of the present application to solve the aforementioned problems is a method of improving insulin resistance, comprising administering a compound represented by the general formula (1), or an organic solvent extract, a hot water extract, or a squeezed solution of a Liliaceae plant, or a fraction thereof, which contains at least 0.001% by dry mass of the compound to a subject whose insulin resistance is to be improved.

In the aforementioned use and method of the present invention, preferred embodiments of the aforementioned compound represented by the general formula (1) are the same as that of the second invention of the present application.

The agent for improving insulin resistance and the food or drink containing the same of the present invention can be administered or ingested in safety, and have preventive effects on lifestyle-related diseases which are considered to be caused by the insulin resistance. In addition, the active ingredient of the agent for improving insulin resistance of the present invention can be ingested in safety from experience, and can easily be produced from available Liliaceae plants such as Aloe vera (Aloe barbadensis Miller).

BRIEF DESCRIPTION OF THE DRAWING

FIG. 1 is a graph showing change in blood glucose level in an insulin tolerance test.

BEST MODE FOR CARRYING OUT THE INVENTION

Next, preferred embodiments of the present invention will be explained in detail. However, the present invention is not limited to the following preferred embodiments and modifications can be freely made within the scope of the present invention. In addition, percentage as used herein indicates percentage by mass unless otherwise specified.

In the present invention, the effect of improving insulin resistance (the effect of enhancing insulin sensitivity) means an effect of preventing or improving various adverse effects on health induced by a decrease in the insulin sensitivity, such as lifestyle-related diseases. Specifically, the agent for improving insulin resistance of the present invention effectively inhibits an increase or production of adipocytokines that elicit insulin resistance, such as plasminogen activator inhibitor (PAI-1), free fatty acid (FFA), tumor necrosis factor (TNF-α), MCP-1, and resistin, and has an effect on reduction of risks, prevention, amelioration, or treatment of the diseases involved in the insulin resistance, such as hyperinsulinemia, hyperlipidemia, abnormal glucose tolerance, diabetes, hypertension, obesity, arteriosclerotic disease, and the like. Thus, the agent for improving insulin resistance of the present invention can be defined as an agent for enhancing insulin sensitivity or an agent for controlling adipocytokine production, in particular, an agent for inhibiting production of adipocytokines that elicits insulin resistance.

There are methods of evaluating insulin resistance such as the glucose clamp method, the steady state plasma glucose (SSPG) method, the minimal model method, a method of evaluating the insulin resistance by calculating homeostasis model assessment insulin resistance (HOMA-IR) from fasting blood glucose level and blood insulin concentration, and the insulin tolerance test. Any of the aforementioned methods can be used for the evaluation of the insulin resistance. However, in the present invention, it is preferred to use the insulin tolerance test using animals, because the test does not affected by insulin secretion property or the like, and thus the insulin sensitivity can be directly investigated.

The compound having the structure represented by the aforementioned general formula (1) has an effect of increasing insulin sensitivity, and thus can prevent or ameliorate diseases caused by the insulin resistance. Therefore, the compound can be used as an active ingredient of the agent for improving insulin resistance or food or drink containing the same. In addition, the insulin sensitivity can also be evaluated by measuring a decrease in blood glucose level after administration of insulin.

The compound used as the active ingredient of the agent for improving insulin resistance of the present invention (hereinafter, also referred to as "the agent of the present invention") is the compound having a structure represented by the aforementioned general formula (1), and any derivatives and the like of the compound are included as the active ingredient as long as they each are the compound having an effect of improving insulin resistance (hereinafter, also referred to as "the compound of the present invention").

It is most preferred that a purity of the compound of the present invention which is used as the active ingredient of the agent for improving insulin resistance of the present invention is 100%. However, the purity can be appropriately set within a range where the agent has the effect of improving insulin resistance.

In addition, the composition which is used as an active ingredient the agent for improving insulin resistance of the present invention (hereinafter, also referred to as "the composition of the present invention") is an extract of a Liliaceae plant or a fraction thereof, which contains the compound having the structure represented by the aforementioned general formula (1) in an amount of at least 0.001% by dry mass, preferably 0.01% by dry mass or more, and more preferably 0.1% by dry mass or more. The upper limit of the content of the compound of the present invention is, but not particularly limited to, preferably 10% by dry mass, 50% by dry mass, 70% by dry mass, or 90% by dry mass, for example.

In the present invention, dry mass means a mass measured after a compound is dried by the drying method defined by "Drying Loss Test" that is a general test method as described in Japanese Pharmacopoeia, Fourteenth Revision, (Mar. 30, 2001, the Japan Ministry of Health, Labor and Welfare, Ministerial Notification No. 111). For example, the mass of the compound of the present invention can be determined in such a manner that: about 1 g of the compound of the present invention is measured off, and dried at 105° C. for 4 hours; and the resultant is cooled by standing in a desicater; and the mass of the compound is weighed with scales.

In the aforementioned general formula (1), R1 represents an alkyl group, or an alkenyl group having 1 or 2 double bonds, which is straight or branched chain having 5 to 16 carbon atoms. In addition, the aforementioned alkyl group and alkenyl group may be a substituted alkyl and alkenyl group having a hydroxyl group and/or a carbonyl group, respectively. R2 and R3 each independently represent a hydrogen atom, an alkyl group or a substituted alkyl group having 1 to 3 carbon atoms, and R4 forms C=O with the carbon atom constituting the ring or represents —OH or —OCOCH$_3$. As the aforementioned alkyl group having 1 to 3 carbon atoms, methyl group, ethyl group and so forth are preferred, and methyl group is particularly preferred.

The aforementioned R1 is preferably any one of the groups represented by the following formulas.

—CH$_2$—CH$_2$—CH(—CH$_2$—CH$_3$)—CH(CH$_3$)$_2$  (i)

—CH$_2$—CH$_2$—CH═C(CH$_3$)$_2$  (ii)

—CH$_2$—CH═C(CH$_3$)—CH(CH$_3$)$_2$  (iii)

—CH$_2$—CH$_2$—C(═CH—CH$_3$)—CH(CH$_3$)$_2$  (iv)

—CH$_2$—CH$_2$—CH(Ra)═C(CH$_3$)Rb  (v)

(wherein Ra and Rb is any of —H, —OH, or —CH$_3$)

—CH$_2$—CH$_2$—CH(Rc)—CH(CH$_3$)Rd  (vi)

(wherein Rc and Rd is any of —H, —OH, or —CH$_3$)

Further, it is preferred that one of R2 or R3 is a hydrogen atom, and the other is a methyl group. Further, it is preferred that R4 is a hydroxyl group.

The most preferred compounds as the aforementioned compound are those represented by the following formulas, 4-methylcholest-7-en-3-ol (formula (2)), 4-methylergost-7-en-3-ol (formula (3)) and 4-methylstigmast-7-en-3-ol (formula (4)).

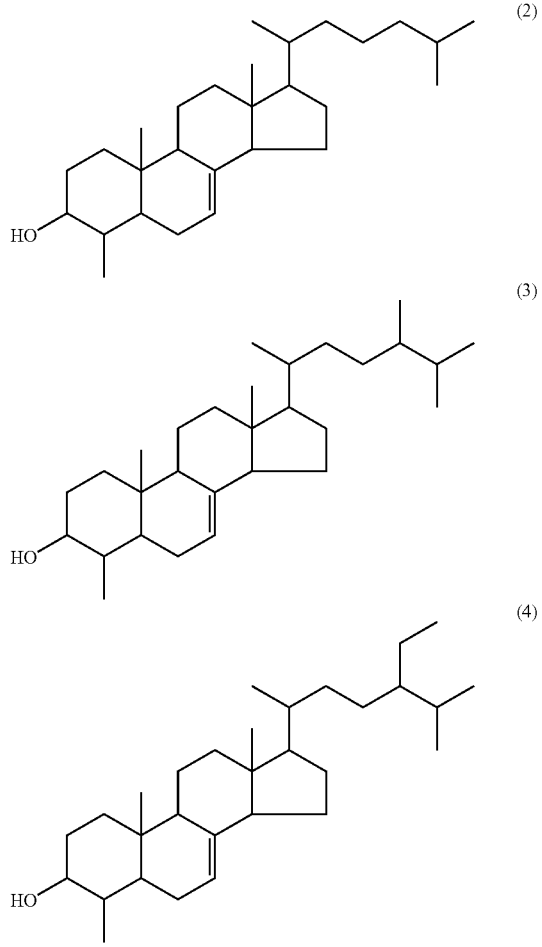

That is, 4-methylcholest-7-en-3-ol is a compound represented by the aforementioned general formula (1) wherein one of R2 and R3 is a hydrogen atom, the other is methyl group, is a hydroxyl group, and R1 is a group represented by the aforementioned formula (vi) (Rc represents —H, and Rd represents —CH$_3$). 4-Methylergost-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (vi) (Rc and Rd both represent —CH$_3$). Further, 4-methylstigmast-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (i).

The agent, food or drink of the present invention may contain one type or two or more arbitrary types of the aforementioned compounds.

It is known that lophenol is contained in plants, and the compound of the present invention can be produced according to the known method for producing lophenol (Yamada A., "Experimental Methods of Biochemistry", Vol. 24, Experimental Methods for Fat and Lipid Metabolism, p. 174, Gakkai Shuppan Center, 1989). The compound of the present invention can be obtained by, for example, extracting the compound from a plant containing the same using a method such as extraction with an organic solvent or extraction with hot water and purifying the obtained extract. In the present invention, although the compound of the present invention may be purified, a composition such as a plant extract or a fraction thereof may also be used so long as it contains an effective amount of the compound.

The compound of the present invention or the composition containing the same can be produced in such a manner that, for example: from a plant belonging to the family Liliaceae, a part or crushed product thereof containing the compound of the present invention, a fraction containing the compound is extracted with an organic solvent or hot water and concentrated.

Examples of the aforementioned plant belonging to the family Liliaceae include plants belonging to the genus *Aloe* or *Allium*. Examples of the plants of the genus *Aloe* include *Aloe vera* (*Aloe barbadensis* Miller), *Aloe ferox* Miller, *Aloe africana* Miller, *Aloe arborescen* Miller var. *natalensis* Berger, *Aloe spicata* Baker and so forth. In the production of the compound of the present invention or a composition containing the same, although the whole of the aforementioned plant may be used, it is preferred to use mesophyll (clear gel portion) thereof. Such a plant or a part thereof is disrupted preferably by using a homogenizer or the like and thereby liquefied, and the compound of the present invention or a composition containing the same is extracted from the disruption product by using an organic solvent or hot water. Examples of the organic solvent include alcohols such as methanol, ethanol and butanol; esters such as methyl acetate, ethyl acetate, propyl acetate and butyl acetate; ketones such as acetone and methyl isobutyl ketone; ethers such as diethyl ether and petroleum ether; hydrocarbons such as hexane, cyclohexane, toluene and benzene; halogenated hydrocarbons such as carbon tetrachloride, dichloromethane and chloroform; heterocyclic compounds such as pyridine; glycols such as ethylene glycol; polyhydric alcohols such as polyethylene glycol; nitrile solvents such as acetonitrile, mixtures of these solvents and so forth. Further, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform:methanol=about 25:1. Further, when a hexane/ethyl acetate mixture (4:1) is used in reverse phase silica gel column chromatography as an elution solvent, the compound of the present invention is eluted in a fraction eluted at an early stage. The obtained fraction can be further purified by HPLC or the like.

Further, the compound used for the present invention may also be produced by a chemical synthesis method or a biological or enzymatic method using microorganisms, enzymes or the like.

Whether a compound or a composition containing the same obtained as described above actually contains the compound of the present invention can be confirmed by, for example, mass spectrometry (MS), nuclear magnetic resonance (NMR) spectroscopy or the like.

The compound of the present invention can be used as an active ingredient of the agent for improving insulin resistance of the present invention and a food or drink containing the same as it is. In addition, an organic solvent extract or a hot water extract of a plant, or a fraction thereof (hereinafter, referred to as "extract etc.") containing the compound of the present invention may be used as the active ingredient of the agent for improving insulin resistance or the food or drink containing the same of the present invention. Furthermore, when Aloe vera belonging to Liliaceae is used as the plant, it is preferable that a total content of aloin and aloe-emodin, which are contained a lot in leaf-skin of Aloe vera, is 5 ppm or less.

The aforementioned extract etc. to be contained in the agent for improving insulin resistance preferably contains at least 0.001% by dry mass, more preferably 0.01 to 1% by dry mass, particularly preferably 0.05 to 1% by dry mass, of the compound of the present invention. Further, the aforementioned extract etc. to be contained in the food or drink preferably contains at least 0.0001% by dry mass, more preferably 0.001 to 1% by dry mass, particularly preferably 0.005 to 1% by dry mass, of the compound of the present invention. The aforementioned extract etc. may contain two or more types of the compound of the present invention. Further, the aforementioned extract etc. may be a solution, or can also be lyophilized or spray-dried in a conventional manner and stored or used as powder.

As the agent for improving insulin resistance of the present invention, the compound of the present invention or a composition containing the same per se, or the compound of the present invention or a composition containing the same combined with a pharmaceutically acceptable carrier can be orally or parenterally administered to a mammal including human. In the agent for improving insulin resistance of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate and hydrobromate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the agent for improving insulin resistance of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual preventive agents for improving insulin resistance as pharmaceutical carriers such as excipients, binders, disintegrating agents, lubricants, stabilizers, flavoring agents, diluents, surfactants and solvents for injection and so forth can be used. Furthermore, so long as the effect of the present invention is not degraded, the compound of the present invention or the extract etc. containing the same can be used in combination with other agents having action of improving insulin resistance.

Although the amount of the compound of the present invention or the extract etc. containing the same contained in the agent for improving insulin resistance of the present invention is not particularly limited and can be suitably selected, the amount may be, for example, at least 0.001% by mass, preferably 0.01 to 1% by mass, particularly preferably 0.05 to 1% by mass, in terms of the amount of the compound of the present invention.

The agent for improving insulin resistance of the present invention can prevent, ameliorate, or treat various diseases, complications, and the like caused by insulin resistance, and reduce the risks of those diseases, complications, and the like. In addition, the agent for improving insulin resistance of the present invention can preferably be used for a patient whose insulin resistance is more aggravated than that of a healthy person. Furthermore, insulin resistance generally means a state where a fasting plasma insulin level is 10 to 15 µU/ml or more, and a HOMA index is 1.73 or more.

Examples of the various diseases caused by insulin resistance include hypertension, hyperlipidemia, diabetes, and arteriosclerotic disease. Examples of the complications caused by the diseases include (a) cerebral stroke, nephrosclerosis, and renal failure caused by hypertension, (b) arteriosclerosis and pancreatitis caused by hyperlipidemia, (c) diabetic retinopathy, nephropathy, neuropathy, and diabetic gangrene caused by diabetes, and (d) cerebral stroke, cerebral infarction, cardiovascular diseases such as angina pectoris and myocardial infarction, and nephropathy such as uremia, nephrosclerosis, and renal failure due to arteriosclerotic disease. In addition, the inventors of the present invention have found that the compound of the present invention has an effect of reducing hemoglobin A1c level and improving hyperglycemia (WO 2005/094838). It is preferred that the diseases to which the agent for improving insulin resistance of the present invention is applied be those not accompanied with higher hemoglobin A1c levels than that of a healthy person.

In addition, the agent of the present invention which has an effect of improving insulin resistance is expected to have an effect of inhibiting production and increase of adipocytokines which elicit the insulin resistance, such as TNF-$\alpha$, MCP-1 and FFA. Therefore, the agent of the present invention has the effect of preventing and/or ameliorating the diseases caused by the increase of the aforementioned adipocytokines, which include autoimmune diseases such as rheumatoid arthritis, Crohn's disease, inflammatory diseases in various organs such as nephritis, pancreatitis, hepatitis and pneumonitis, angiopathy, sepsis, cancer cachexia. Thus, the agent for improving insulin resistance of the present invention can preferably be used for a patient in which the production of the adipocytokines is enhanced, in particular, a patient in which the production of the adipocytokines that elicit the insulin resistance is enhanced.

The administration time of the agent of the present invention is not particularly limited and can be suitably selected according to the method for treating an objective disease. Furthermore, the administration route is preferably determined depending on the dosage form, age, sex and other conditions of patients, severity of symptoms of patients and so forth. The dose of the active ingredient in the agent of the present invention is suitably selected depending on the dose regimen, age and sex of patients, severity of disease, other conditions of patients and so forth. The amount of the compound of the present invention as an active ingredient is usually selected from the range of, preferably 0.001 to 50 mg/kg/day, more preferably 0.01 to 1 mg/kg/day, as a tentative dose. Furthermore, when the extract etc. containing the compound of the present invention is used, the dry weight of the extract etc. is selected from the range of, preferably 0.1 to 1000 mg/kg/day, more preferably 1 to 100 mg/kg/day, as a tentative amount. In any case, the dose can be administered once daily or several times as divided portions.

The compound of the present invention or the composition containing the same can be added to food or drink (a drink or a food) to produce, a food or drink having an effect of improving insulin resistance. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added. The amount of the compound of the present invention or the extract etc. containing the same contained in the food or drink of the present invention is not particularly limited and can be suitably selected. For example, the compound of the present invention or the extract etc. containing the same is contained in the food or drink in an amount of at least 0.0001% by mass, preferably 0.001 to 1% by mass, particularly preferably 0.005 to 1% by mass, in terms of the amount of the compound of the present invention.

The food or drink of the present invention can be applied to various uses which utilize the effect of improving insulin resistance. For example, the food or drink of the present invention can be used for reduction and remove of risk factors of the lifestyle-related diseases which are considered to be due to the insulin resistance. In addition, the food or drink of the present invention can prevent the diseases caused by insulin resistance such as hypertension, hyperlipidemia, and diabetes, and can reduce the risks of those diseases. Further, the food or drink of the present invention can prevent various complications caused by the insulin resistance such as cerebral stroke, nephrosclerosis, renal failure caused by hypertension, arteriosclerosis, pancreatitis, and the like due to hyperlipidemia, diabetic retinopathy, nephropathy, neuropathy, diabetic gangrene caused by diabetes, cerebral stroke, cerebral infarction, cardiovascular diseases such as angina pectoris and myocardial infarction, nephropathy such as uremia, nephrosclerosis, and renal failure due to atherosclerotic disease, and can reduce risks of those diseases.

In addition, the food or drink of the present invention is expected to have an effect of inhibiting production and increase of the adipocytokines that elicit insulin resistance, such as TNF-$\alpha$, MCP-1, and FFA. Therefore, the agent of the present invention has an effect of preventing the diseases and decreasing risks of these diseases caused by the increase of the aforementioned adipocytokines, which include autoimmune diseases such as rheumatoid arthritis, Crohn's disease, inflammatory diseases in various organs such as nephritis, pancreatitis, hepatitis, and pneumonitis, angiopathy, sepsis, cancer cachexia. Thus, the food or drink of the present invention can preferably be ingested by a patient in which the production of the aforementioned adipocytokines is enhanced, in particular, a patient in which the production of the adipocytokines that elicit the insulin resistance is enhanced.

The food or drink of the present invention is preferably marketed as a food or drink attached with an indication that the food or drink is used for improving insulin resistance, for example, "food or drink containing a compound having an effect of improving insulin resistance indicated as 'For improving insulin resistance'", "food or drink containing a plant extract indicated as 'For improving insulin resistance'", or "food or drink containing an *Aloe vera* extract indicated as 'For improving insulin resistance'" and the like. In addition, because the compound of the present invention and the composition and the like containing the same have an effect of improving insulin resistance, and the indication of "improving insulin resistance" is thus considered to have a meaning that insulin sensitivity is enhanced. Therefore, the food or drink of the present invention can be indicated as "For enhancing insulin sensitivity". In other words, the indication of "For improving insulin resistance" may be replaced by the indication of "For enhancing insulin sensitivity".

The wording used for such an indication as mentioned above is not limited to the wording "For improving insulin resistance" or "For enhancing insulin sensitivity". Other wordings are also encompassed within a scope of the present invention as long as the wordings notify the effect of enhancing insulin sensitivity, or preventing or improving insulin resistance. For the wordings, indications based on various uses, which notify consumers that the food or drink has an effect of improving insulin resistance or enhancing insulin sensitivity. Examples of the indication include "Suitable for those who tend to be insulin resistance" and "Useful for reducing or removing risk factors (risks) of lifestyle-related diseases".

The aforementioned term "indication" includes all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth. On the other hand, the indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, other documents and so forth.

Examples of the indication further include indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

The present invention will be explained more specifically with reference to the following examples. However, the scope of the present invention is not limited to the following examples.

First, it is explained by Preparation Example that the compound or composition of the present invention can be produced from a plant belonging to a Liliaceae.

PREPARATION EXAMPLE 1

In an amount of 100 kg of mesophyll (clear gel portion) of *Aloe vera* was liquefied by using a homogenizer, added with 100 L of an ethyl acetate/butanol mixture (3:1) and stirred.

The mixture was left standing overnight, and then the ethyl acetate/butanol mixture and the aqueous layer were separated to recover the ethyl acetate/butanol mixture. The extract from this ethyl acetate/butanol mixture obtained by concentrating the ethyl acetate/butanol mixture under reduced pressure weighed 13.5 g. A solution of 13 g of this extract dissolved in 1 mL of a chloroform/methanol mixture (1:1) was loaded on a column filled with 400 g of Silica Gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. It was confirmed by normal phase and reverse phase thin layer chromatography (Merck Ltd., Silica Gel 60F254 and RP-18F2543) that, among these fractions, the compound of the present invention existed in the fraction eluted with the mixture of chloroform:methanol=25:1.

This crude purified substance (crude purification product 1) containing the compound of the present invention weighed 3 g. Further, the yields of the crude purification products obtained in the above operation from the fractions eluted with the mixtures of chloroform:methanol=10:1 and 1:1 were 1.17 and 2.27 g, respectively. The solvents of these fractions were removed, then each extract was dissolved in 1 mL of a chloroform/methanol mixture (1:1) and loaded on a column filled with 100 g of Silica Gel 60 to attain adsorption of the components to the column, and then the components were eluted with 1100 mL of a hexane/ethyl acetate mixture (4:1). The eluted fractions were collected as aliquots of 300 mL (fraction A), 300 mL (fraction B) and 500 mL (fraction C) in this order. The yields obtained after removing the solvents from the fractions A, B and C were 0.6 g, 1.35 g and 0.15 g, respectively. It was confirmed by normal phase and reverse phase thin layer chromatography that the compound of the present invention had been concentrated in the fraction A (crude purification product 2). This crude purification product 2 was further separated by HPLC using COSMOSIL C18 (Nacalai Tesque, Inc.) with a chloroform/hexane mixture (85: 15) to obtain 1.3 mg of compound 3 (4-methylcholest-7-en-3-ol), 1.2 mg of compound 4 (4-methylergost-7-en-3-ol) and 1 mg of compound 5 (4-methylstigmast-7-en-3-ol). The structures of these compounds were confirmed by MS and NMR.

EXAMPLE 1

The present example was performed by using AKR mice to which insulin resistance was induced by feeding the mice with a high-fat diet, to evaluate the change in the level of free fatty acid (FFA) in serum, which was caused by an application of the agent of the present invention for improving insulin resistance.

(1) Preparation of Samples

Compound 3 (4-methylcholest-7-en-3-ol), Compound 4 (4-methylergost-7-en-3-ol), and Compound 5 (4-methylstigmast-7-en-3-ol) which were produced in Preparation Example 1 were each dissolved in DMSO and adjusted with distilled water to each have a concentration of 1 µg/ml, to thereby prepare Test Samples 1, 2, and 3. In this case, DMSO was adjusted to have a final concentration of 0.2%. In addition, a solution without the test samples was prepared as a negative sample.

(2) Test Method 6-week-old male AKR mice (purchased from The Jackson Laboratory, US) were preliminarily fed with a high-fat diet (Research Diet Inc.) for 2 months to induce thereto insulin resistance. After that, the mice were divided into groups of 8 mice each. Each of the groups of mice were orally administered with 1 ml per 40 g of body weight (25 µg/kg of body weight) of a test sample or the negative sample once a day using a sonde. At 60th day from the initiation of the administration of the samples, blood was collected from the mice under fasting, and the level of the free fatty acid in serum were measured by using a NEFA C-test Wako (Wako Pure Chemical Industries, Ltd.).

(3) Results (Level of Free Fatty Acid in Blood)

Table 1 shows level of the free fatty acid in mouse serum at the 60th day from the initiation of the administration. As compared with the group administered with the negative sample, it was observed that administration of Test samples 1, 2, and 3 was tend to reduce the free fatty acid levels in serum to 86.4%, 81.6%, and 60.8%, respectively. Therefore, it was found that the administration of the agent for improving insulin resistance of the present invention reduces systemic concentrations of the free fatty acid and thus exhibits a preventive effect on aggravation of insulin resistance.

TABLE 1

| Sample | Free fatty acid (mEp/l) | Test sample/negative sample (%) |
|---|---|---|
| Test Sample 1 | 1.35 ± 0.23 | 84.5 |
| Test Sample 2 | 1.21 ± 0.22 | 81.6 |

TABLE 1-continued

| Sample | Free fatty acid (mEp/l) | Test sample/negative sample (%) |
|---|---|---|
| Test Sample 3 | 0.90 ± 0.15 | 60.8 |
| Negative sample | 1.48 ± 0.17 | — |

EXAMPLE 2

The present example was performed by using AKR mice to which insulin resistance was induced by feeding with a high-fat diet, to evaluate the effects of the agent for amelioration insulin resistance of the present invention on production of TNF-α and MCP-1 from respective cells of fat tissues.

(1) Preparation of Samples

In Example 2, the same test samples and negative sample as those prepared in Example 1 were used.

(2) Test Method 6-week-old male AKR mice (purchased from The Jackson Laboratory US) were preliminarily fed with a high-fat diet (Research Diet Inc.) for 2 months to induce thereto insulin resistance. After that, the mice were divided into groups of 8 mice each. Each of the groups of mice was orally administered with 1 ml per 40 g of body weight (25 μg/kg of body weight) of a test sample or the negative sample once a day using a sonde. At 60th day from the initiation of the administration of the samples, epididymal fat tissues were collected from the mice under fasting, and 1 g of each of the fats was added with 1.5 ml of a D-MEM/F12 medium containing 0.5% bovine serum albumin, followed by culturing at 37° C. After 1 hour of the culture, culture supernatants were collected, and concentrations of TNF-α and MCP-1 in the culture supernatants were measured by ELISA (Biosource).

(3) Results (Amounts of Produced TNF-α and MCP-1)

Table 2 shows the amounts of TNF-α produced by the fat tissues, and Table 3 shows the amounts of MCP-1 produced by the fat tissues. As apparent from the results thereof, the groups administered with Test Samples 1, 2, and 3, respectively, were confirmed to have significant inhibitory effects on the production of both of TNF-α and MCP-1 as compared with the group administered with the negative sample. As the results of the present example, it was found that the administration of the agent for improving insulin resistance of the present invention reduces the production of adipocytokines that elicit the insulin resistance in the fat tissues and aggravate the insulin resistance, and the elicit of the insulin resistance is thus prevented. In addition, p values in the tables indicate significance probability by Tukey-Kramer's test.

TABLE 2

| Sample | TNF-α (pg/ml) | p value |
|---|---|---|
| Test Sample 1 | 33.73 ± 1.68* | 0.0450 |
| Test Sample 2 | 32.71 ± 1.70* | 0.0170 |
| Test Sample 3 | 29.80 ± 3.82* | 0.0157 |
| Negative sample | 37.89 ± 2.56 | — |

In the Table,
*indicates that there was a statistically significant inhibitory effect on TNF-α production.

TABLE 3

| Sample | MCP-1 (pg/ml) | p value |
|---|---|---|
| Test Sample 1 | 100.86 ± 8.31* | 0.0154 |
| Test Sample 2 | 95.56 ± 10.56* | 0.0043 |
| Test Sample 3 | 87.80 ± 9.24* | 0.0017 |
| Negative sample | 122.92 ± 10.06 | — |

In the Table,
*indicates that there was a statistically significant inhibitory effect on MCP-1 production.

EXAMPLE 3

The present example was performed by using AKR mice to which insulin resistance was induced by feeding with a high-fat diet, to confirm an enhancing effect of the agent for improving insulin resistance of the present invention on insulin sensitivity by performing an insulin tolerance test.

(1) Preparation of Samples

In Example 3, the same test samples and negative sample as those prepared in Examples 1 and 2 were used.

(2) Test Method 6-week-old male AKR mice (purchased from The Jackson Laboratory, US) were preliminarily fed with a high-fat diet (Research Diet Inc.) for 2 months to induce thereto insulin resistance. After that, the mice were divided into groups of 8 mice each. Each of the groups of mice was orally administered with 1 ml per 40 g of body weight (25 μg/kg of body weight) of a test sample or the negative sample once a day using a sonde. At 45th day from the initiation of the administration of the samples, an insulin tolerance test was performed. The insulin tolerance test in the present example was performed in such a manner that: the mice were fasted for 4 hours, and were then intraperitoneally administered with 0.75 U/kg of body weight of a human insulin (Eli Lily and Company); and changes with time in blood glucose level were measured from the initiation of the administration of insulin to after 60 minutes later.

(3) Results (Insulin Tolerance Test)

The results of the present example were as shown in FIG. 1 which shows the results of the insulin tolerance test. As apparent from FIG. 1, the groups administered with Test Sample 1, 2, and 3, respectively, exhibited rapid reduction in blood glucose levels thereof immediately after the initiation of the administration of insulin as compared with the group administered with the negative sample. From the results of the present example, it was revealed that the administration of the agent for improving insulin resistance of the present invention enhances the insulin sensitivity.

INDUSTRIAL APPLICABILITY

The present invention can provide an agent for improving insulin resistance which is safe without side effects and is capable of enhancing insulin sensitivity, and can provide a physiologically functional food or drink such as foods for specified health uses containing the agent for improving insulin resistance. The agent for improving insulin resistance and the physiologically functional food or drink containing the same of the present invention have improving or preventive effects on diseases, complications and the like caused by a decrease of insulin sensitivity, for example the lifestyle-related diseases such as hypertension, diabetes, hyperlipidemia, and arteriosclerosis, and have reducing effects on risks of those diseases, complications, and the like.

What is claimed is:

1. A method for treating hyperinsulinemia or abnormal glucose tolerance, which comprises administering an ethyl acetate/butanol mixture (3:1) extract or a chloroform/methanol mixture (2:1) extract of mesophyll of *Aloe vera* (*Aloe barbadensis* Miller), or a fraction thereof, which comprises at least 0.001% by mass of a compound selected from the group consisting of 4-methyl-cholest-7-en-3-ol, 4-methyl-ergost-7-en-3-ol, and 4-methyl-stigmast-7-en-3-ol, to a subject whose hyperinsulinemia or abnormal glucose tolerance is to be treated.

2. A method for treating hyperinsulinemia or abnormal glucose tolerance, which comprises administering at least 0.001% by mass of a compound selected from the group consisting of 4-methyl-cholest-7-en-3-ol, 4-methyl-ergost-7-en-3-ol, and 4-methyl-stigmast-7-en-3-ol, to a subject whose hyperinsulinemia or abnormal glucose tolerance is to be treated.

* * * * *